United States Patent
Lessure et al.

(10) Patent No.: US 6,576,905 B2
(45) Date of Patent: Jun. 10, 2003

(54) METHOD AND ASSEMBLY FOR GAS DETECTION VIA A CONVERGENT BIREFRINGENT FILTER

(75) Inventors: Harold S. Lessure, Pittsburgh, PA (US); Richard A. Evans, Pittsburgh, PA (US); Richard P. Kunkle, Irwin, PA (US); Dale M. Matuza, Murrysville, PA (US)

(73) Assignee: Gas Research Institute, Des Plaines, IL (US)

( * ) Notice: Subject to any disclaimer, the term of this patent is extended or adjusted under 35 U.S.C. 154(b) by 0 days.

(21) Appl. No.: 09/881,644

(22) Filed: Jun. 14, 2001

(65) Prior Publication Data

US 2003/0030811 A1 Feb. 13, 2003

(51) Int. Cl.[7] .................................................. G01B 9/02

(52) U.S. Cl. .............................. 250/338.5; 250/339.07; 250/339.08; 356/346; 356/352

(58) Field of Search ................................. 356/346, 352, 356/437; 250/338.5, 339.07, 339.08

(56) References Cited

U.S. PATENT DOCUMENTS

| 4,195,931 A | | 4/1980 | Hara |
|---|---|---|---|
| 4,998,017 A | | 3/1991 | Ryan et al. |
| 5,076,699 A | | 12/1991 | Ryan et al. |
| 5,418,615 A | * | 5/1995 | Doyle .......................... 356/436 |
| 5,946,095 A | * | 8/1999 | Henningsen et al. ........ 356/346 |

OTHER PUBLICATIONS

Amnon Yariv: *Optical Electronics*3rd Edition, Chapter 9, 274–305, Holt, Rinehart and Winston, (1985).
Eugene Hecht and Alfred Zajac: *Optics*, 263–266, Addison–Wesley Publishing Company, Reading, Massachusetts, (1974).
Bruce H. Billings: *A Tunable Narrow–Band Optical Filter*, Journal of the Optical Society of America, vol. 37, No. 10, 738–746, Oct. 1947.
John W. Evans: *The Birefringent Filter*, Journal of the Optical Society of America, vol. 39, No. 3, No. 3, 229–242, Mar. 1949.
Alan M. Title and William J. Rosenberg: *Tunable Birefringent Filters*, Optical Engineering, vol. 20, No. 6, 185–823, Nov./Dec. 1981.
E. Mascart: *Sur les Modification Qu'Eprove la Lumiere, Annales scientifiques de l'Ecole Normale superieure*, vol. 3, pp. 395–399, 1874.
Fabry and Perot: *Sur la constitution des raies jaunes du sodium, Comptes Rendus*, vol. 130, pp. 653–655, 1900.
Bernard Lyot: *Le Filtre Monochromatique Polarisant et ses Applications en Physique Solaire, Annales D'Astrophysique*, vol. 7, No. 1–2, pp. 31–79, 1944.

* cited by examiner

Primary Examiner—John R. Lee
Assistant Examiner—David A. Vanore
(74) Attorney, Agent, or Firm—Mark E. Fejer

(57) ABSTRACT

An assembly and method provide sensitive high speed spectroscopic gas detection via the use of a non-collimated convergent light path through a birefringent crystal in a birefringent filter design to allow improved light collection and a reduction in the number of optical elements required to produce a useful absorption signal for the detection of gases.

20 Claims, 3 Drawing Sheets

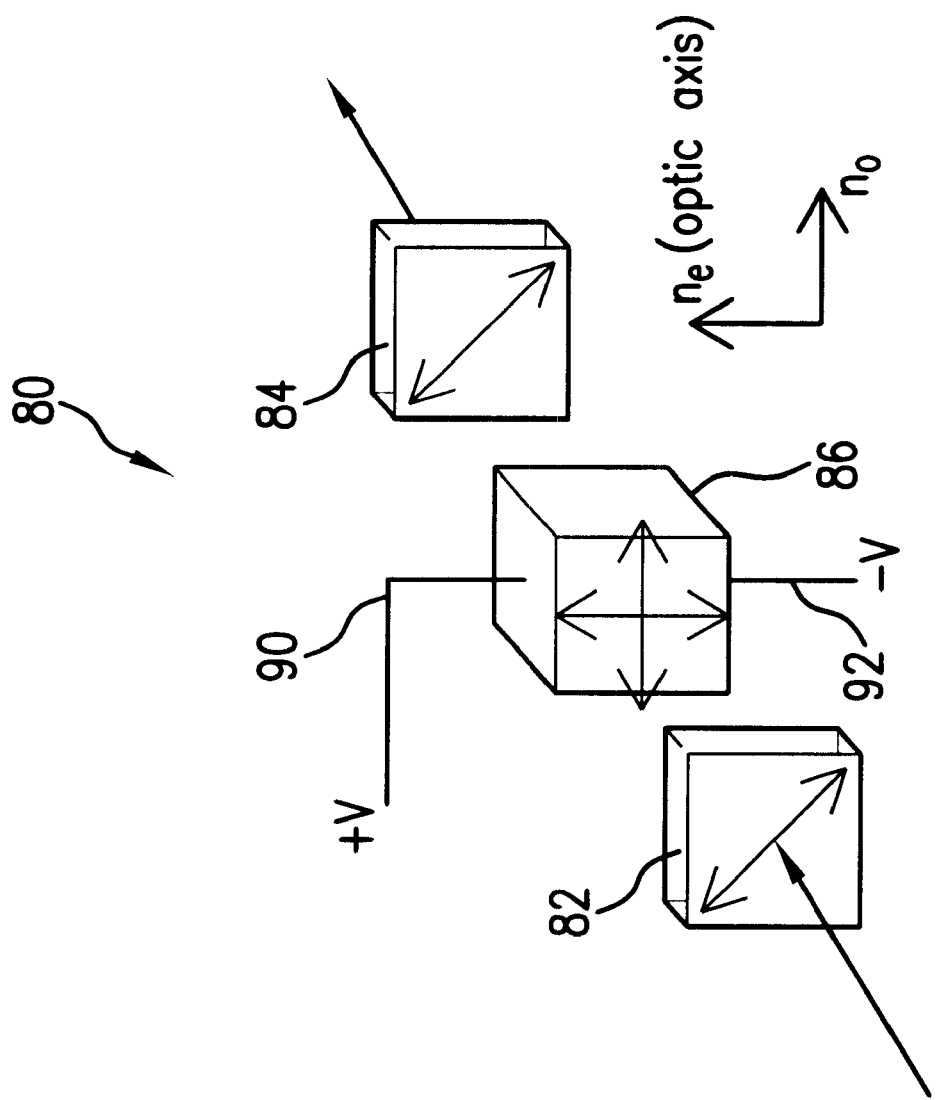

METHOD AND ASSEMBLY FOR GAS DETECTION VIA A CONVERGENT BIREFRINGENT FILTER

BACKGROUND OF THE INVENTION

This invention relates generally to optical filtering and, more particularly, to optical filtering for chemical identification such as gas detection.

It is well known to detect, measure and/or analyze the characteristics of a fluid mixture, such as composed of a gas, liquid or mixture thereof, via evaluation of the absorption spectra obtained via optical methods. Birefringent filters have been used for a variety of diverse applications, including emission spectrum filtering of sodium doublet D lines and electro-optical modulators. The basic operation of such devices is described in various textbooks including Amnon Yariv, *Optical Electronics*, $3^{rd}$ Edition, Holt, Rinehart and Winston, chapter 9, (1985) and Eugene Hecht and Alfred Zajac, *Optics*, Addison-Wesley Publishing Company, Reading, Mass., pp 263–266, (1974), for example and the disclosures of which are hereby incorporated in their entirety.

Typically, light is collimated prior to being projected through a birefringent filter to ensure a uniform phase modulation across the aperture of the incoming beam. A problem with using birefringent filters in collimated light is that the collimating process can be inefficient in collecting the light thus making it difficult to produce corresponding assemblies or devices having relatively low power consumption requirements, such as may be suitable or desired in particular applications such as for portable or battery-powered gas detection instruments.

In view of the above, there is a need and a demand for improved gas detection assemblies and methods such as permit or allow for a more efficient use of light. Further, there is a need and a demand for improved gas detection assemblies and methods such as eliminate the need for collimating optics and allows for a higher throughput of light while reducing or minimizing the number of required optical elements.

SUMMARY OF THE INVENTION

A general object of the invention is to provide an improved assembly and method for detecting a target species in a selected sample.

A more specific objective of the invention is to overcome one or more of the problems described above.

The general object of the invention can be attained, at least in part, through an assembly which includes a source of convergent electromagnetic radiation spaced apart from a tunable birefringent filter by a sample volume. The assembly also includes at least one detector to detect the incidence of electromagnetic radiation of a selected wavelength after passage of convergent electromagnetic radiation through the sample volume and the birefringent filter.

The prior art generally fails to provide suitably low power consuming assemblies and methods such as for use in the detection of a target species in a test sample. Further, the prior art has generally failed to provide such detection assemblies and methods having either or both a construction or an operation which is as simple as may be desired. Consequently, the prior at has generally failed to provide such detection assemblies and methods which are as conducive to portable operation and use as has been desired.

The invention further comprehends an improvement in a method for detecting the presence of a target species in a sample volume wherein light is passed through the sample volume to a birefringent filter. In accordance with a preferred embodiment of the invention, the improvement of the invention involves passing convergent light rays through the sample volume to the birefringent filter.

The invention still further comprehends a method for detecting the presence of a target species in a gas sample, wherein the target species absorbs light in a predetermined spectral region. In accordance with one preferred embodiment of the invention, such a method involves passing convergent light through the gas sample to a birefringent filter and subsequently to a detector. The birefringent filter is tuned through the predetermined spectral region and a signal is produced representing the presence of the target species in the gas sample.

As used herein, references to a "convergent birefringent filter" or the like are to be understood to refer to a birefringent filter in or through which noncollimated, preferably convergent, light is passed.

Other objects and advantages will be apparent to those skilled in the art from the following detailed description taken in conjunction with the appended claims and drawings.

BRIEF DESCRIPTION OF THE DRAWINGS

FIG. 4 is a simplified schematic of an electro-optic birefringent filter wherein an applied voltage is used to induce a modulating electric field and tune the filter transmission.

DETAILED DESCRIPTION OF THE INVENTION

The present invention provides improved assemblies and methods for detecting a target species in a selected sample or sample volume. Further, as described below, the present invention can be embodied in a variety of different structures or assemblies.

For uniaxial crystals, the polarization of an incoming beam of electromagnetic radiation, e.g., light, is set to be incident on the crystal at 45 degrees to the optic axis in the plane of the input face of the crystal. An incoming ray of light is then resolved into two rays having orthogonal polarizations. These rays are referred to as the ordinary ray (o-ray) and the extraordinary ray (e-ray). The ordinary ray propagates with a velocity $c/n_o$ and a polarization normal to the optic axis. The extraordinary ray propagates with a velocity $c/n_e$ and with a polarization parallel to the optic axis. In an electro-optic crystal, the index of refraction can be selectively and desirably varied by applying a voltage to the crystal in the appropriate orientation. The two rays propagate with differing velocities and emerge from the crystal output face with a phase difference produced by the optical path length difference $\psi$ between the two rays. The optical path length difference between the ordinary and extraordinary rays is given by Equation (1), below:

$$\psi = n_o L - n_e L = L(n_o - n_e) \quad (1)$$

and the filter transmission is a sinusoidal function of $2\pi/\lambda$ given by Equation (2), below:

$$T(\lambda, \psi) = \cos^2\left(\frac{\pi\psi}{\lambda}\right) = \frac{1}{2}\cos\left(\frac{2\pi\psi}{\lambda}\right) + \frac{1}{2} \quad (2)$$

such that the transmission is periodic with $2\pi/\lambda$ and $\psi$ and is selectively and desirably varied through variations in $\psi$ induced by the applied voltage.

The phase difference depends on the path of propagation of the rays in the crystal and any variation of the refractive indices which could be induced (such as by the application of an electric field, for example). The resulting modification of the phase difference is generally given by Equation (3) below:

$$\psi + \Delta\psi = L[n_o - n_e + \Delta(n_o - n_e)] + \Delta L(n_o - n_e) \quad (3)$$

This modified optical path length produces a change in the transmission $T(\lambda, \psi)$ of the filter when averaged over the bundle of light rays traversing the birefringent crystal according to Equation (2).

Figure 1:
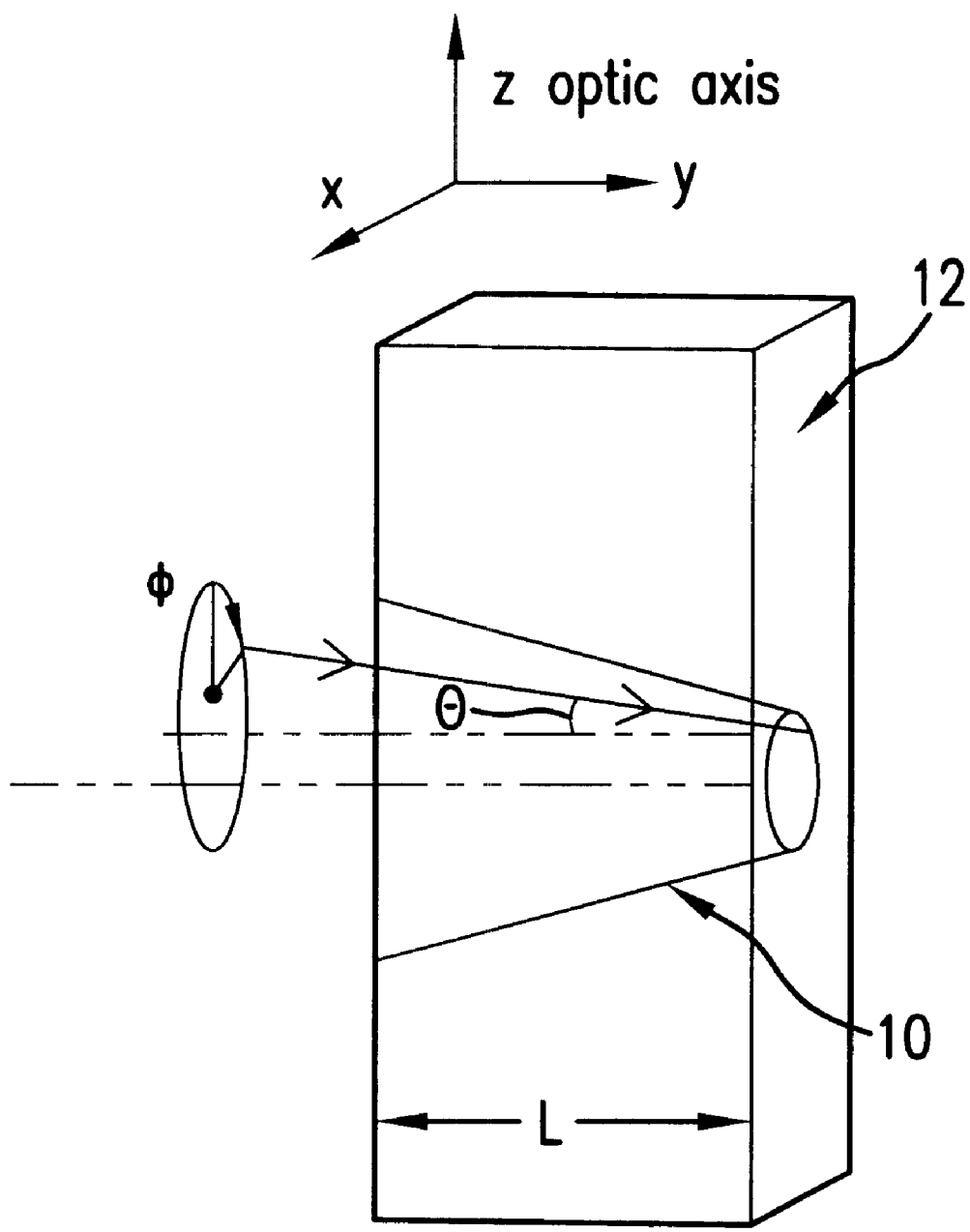
FIG. 1 is a simplified schematic illustrating a convergent light cone traversing a birefringent filter.

Turning now to FIG. 1, there is shown a bundle of rays in a convergent cone of electromagnetic radiation, e.g., light, generally designated by the reference numeral 10, in a birefringent crystal 12. Those skilled in the art and guided by the teachings herein provided will appreciate that various birefringent materials having suitable electro-optic effects can be used in the practice of the invention. For example and without unnecessarily limiting the broader practice of the invention, suitable birefringent materials for use in the practice of the invention may include lithium niobate, ammonium dihydrogen phosphate (ADP), potassium dihydrogen phosphate (KDP), lithium tantalate, zinc selenide and birefringent liquid crystals. As will be appreciated, the selection of an appropriate birefringent material for a particular application will generally be dependent on factors such as the desired assembly geometry and particular light wavelengths of interest.

An incoming light ray is resolved into ordinary and extraordinary polarization components as it enters the crystal 12. Each ray of light propagates in the crystal 12 with a pathlength determined by the crystal thickness L, the direction of the incoming ray and the appropriate index. The ordinary ray component will travel with the constant index $n_o$. The extraordinary ray component (e-ray) travels with an index $n_e$ which depends on the e-ray direction in general accordance with Equation (4) below:

$$\frac{1}{n_e^2(\alpha)} = \frac{\sin^2\alpha}{n_e^2} + \frac{\cos^2\alpha}{n_o^2} \quad (4)$$

where $\alpha$ is the angle between the e-ray wave vector and the optic axis. The general ray direction incident on the crystal 12 can be specified with two angles: the polar angle $\theta$ and the azimuthal angle $\Phi$ as shown in FIG. 1.

For the bundle of rays traveling in the crystal in different directions, the average optical path difference over the cone can be expressed as Equations (5) and (6) below:

$$<\psi> = \int\int_{cone} (\psi + \Delta\psi) d\theta d\phi \quad (5)$$

or $$<\psi> = \int\int_{cone} L(\theta, \phi)[n_o - n_e(\theta, \phi) + \Delta(n_o - n_e(\theta, \phi))] + \Delta L(\theta, \phi)(n_o - n_e(\theta, \phi)) d\theta d\phi \quad (6)$$

The average filter response with the cone of convergent rays $<T(\lambda)>$ is then given by the resulting integrated optical path length, $<\psi>$ in accordance with Equation (2), as shown by Equation (7) below:

$$<T(\lambda)> = \int\int_{cone} \cos^2\left(\frac{\pi\psi}{\lambda}\right) d\theta d\phi \quad (7)$$

The average optical path difference over the cone, $<\psi>$, is or can be made dependent on a variety of physical environmental variables or parameters including, for example: wavelength, light intensity, temperature, pressure, orientation, electric field and magnetic field. Any of these variables or parameters can be appropriately varied to effect modulation of the filter transmission response. Guided by the teachings herein provided, those skilled in the art will appreciate that wavelengths of interest and selected modulation schemes will generally determine the selection of light or electromagnetic radiation source, lenses, mirrors, optical filters, polarizers, birefringent crystal, modulation apparatus, detectors, detection scheme and electronics for appropriate and desired operation. It will also be understood that since a birefringent filter has a periodic filter response, the period of the filter can optionally be designed to match a set or subset of absorption lines of a target absorbing species, if desired.

A specific expected or contemplated use for a convergent beam spectroscopic filter, in accordance with a preferred embodiment of the invention, is in the sensing of the presence of a particular or specific light absorbing material, such as a particular or specific gas which has optical absorption in the range of tunability of the filter. In accordance with a preferred embodiment of the invention, a convergent beam birefringent filter is appropriately tuned through the spectral region where absorption takes place due to the presence of the absorbing species. The presence of the absorbing species, such as in a selected test sample volume, causes a reduction in transmitted light. Such reduction in transmitted light can be read by one or more detectors as a quantitative determination of the absorbing species. The tuning can be rapid and/or periodic in time to create an absorption signal suitable for phase sensitive detection.

Figure 2:
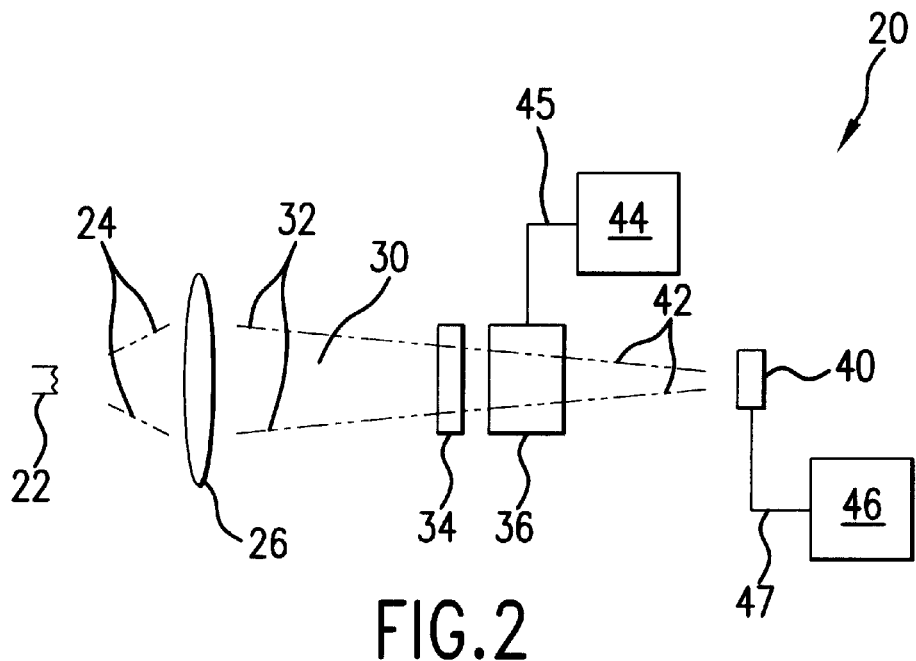
FIG. 2 is a simplified schematic of a convergent beam birefringent detection assembly in accordance with one preferred embodiment of the invention.

FIG. 2 illustrates a convergent beam birefringent detection assembly 20 in accordance with one preferred embodiment of the invention. The detection assembly 20 includes a source of electromagnetic radiation 22 to provide a supply of light, as signified by the lines 24. The detection assembly 20 further includes an optical element 26 to direct the light in a converging beam. The optical element 26 may, for example, be either a transmitting element such as a lens or a reflecting element such as a mirror. Those skilled in the art and guided by the teachings herein provided will appreciate that the selection, incorporation and use of specific optical elements may depend on various factors including but not limited to availability and the specifically desired assembly geometry, for example.

The light passing through the optical element 26 defines a light path 30, schematically outlined by the lines 32, and into which light path a volume of a selected sample or test material (not shown) can be placed such that the presence of an absorbing species in the sample can be detected. If desired and as shown, a filter 34 may be included to assist in defining a spectral region of interest within the spectrum of the source. For example, a filter may be selected and used to limit light transmitted therethrough to the light in that part of the optical spectrum that is of interest. Suitable filters may include multilayer dielectric interference filters, for example, and may include means for temperature control to facilitate operation at desired wavelengths.

In accordance with a preferred embodiment of the invention, a birefringent filter 36 is positioned in the convergent optical beam. As will be appreciated by those skilled in the art guided by the teachings herein provided and as described in greater detail below, birefringent filters in assemblies in accordance with the invention may contain or be composed of one or more elements or stages such as may be desired to more specifically limit or restrict the light passed therethrough.

The light is then incident on a detector 40, as signified by the lines 42. The detector 40 can be of any type appropriate for the radiation to be detected and may include suitable temperature control, such as via a thermoelectric cooler. Those skilled in the art and guided by the teachings herein provided will appreciate that various detectors are available and can desirably be used in the practice of specific embodiments of the invention. For example and without necessarily limiting the broader practice of the invention, suitable detectors of electromagnetic radiation such as may desirably be used in the practice of the invention include photodiodes, pyroelectric detectors, photomultiplier tubes, bolometers, photoconductive detectors, thermopiles or other optic or thermal detectors.

In accordance with a preferred practice of the invention, the detection assembly may also desirably include or contain suitable control components, such as in the form of electronics such as represented by the box 44 and joined or connected to the birefringent filter 36 as signified by the line 45. Those skilled in the art and guided by the teachings herein provided will appreciate that suitable control components for use in the practice of the invention may desirably serve to one or more produce heat, control the temperature of the instrument and/or tune the transmission of the birefringent filter. For example, suitable components to either or both produce heat and assist in temperature control may include a heater, such as in the form of a resistor, and such as in intimate contact with the associated birefringent filter.

The detection assembly may also desirably include or contain suitable components, such as in the form of a suitable display device to permit the display or read out of a signal which represents the absorption due to the presence of the target absorbing species in the light path. Such a display device is represented by the box 46, joined or connected to the detector 40 as signified by the line 47.

Figure 3:
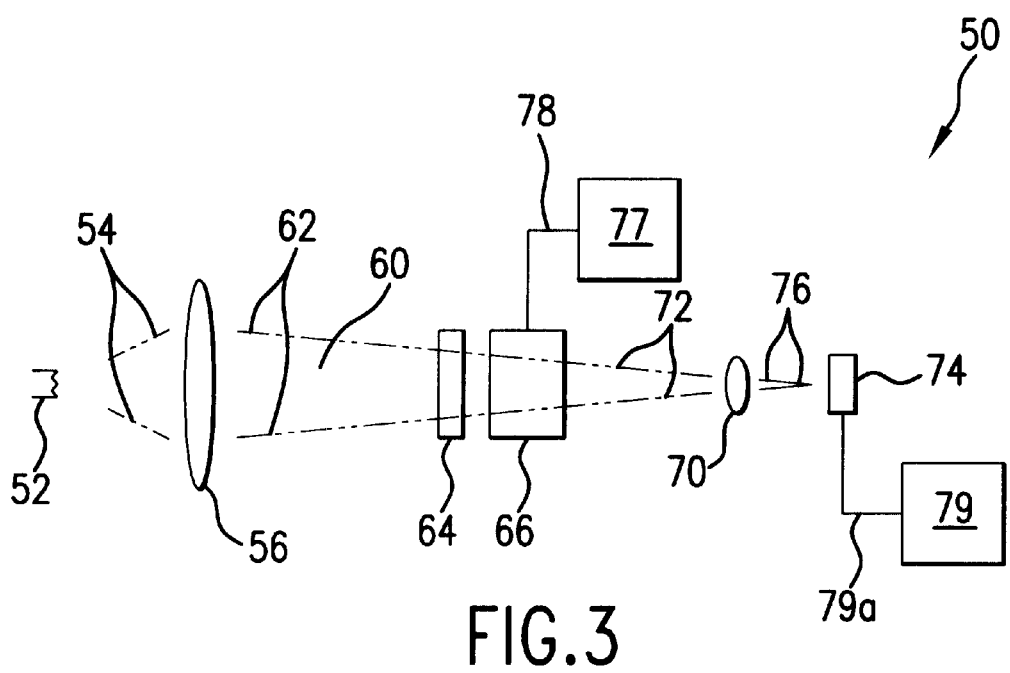
FIG. 3 is a simplified schematic of a convergent beam birefringent detection assembly in accordance with another preferred embodiment of the invention.

FIG. 3 illustrates, in accordance with another preferred embodiment of the invention, a convergent beam birefringent detection assembly, generally designated by the reference numeral 50. The detection assembly 50 is generally similar to the detection assembly 20 described above. For example, the detection assembly 50, similar to the detection assembly 20, includes a source of electromagnetic radiation 52 to provide a supply of light (signified by the lines 54). The detection assembly 50 also includes an optical element 56 to direct the light in a converging beam light path 60, schematically outlined by the lines 62, and into which light path a volume of a selected sample or test material (not shown) can be placed such that the presence of an absorbing species in the sample can be detected. The detection assembly 50 also includes an optional filter 64 to define a spectral region of interest within the spectrum of the source and a birefringent filter 66 in the convergent optical beam.

The detection assembly 50 differs from the detection assembly 20 in that the detection assembly 50 also includes a second optical element 70 to assist in directing the light signal emanating from the birefringent filter 66, signified by the lines 72, more precisely onto the detector 74, as signified by the lines 76. Such second optical element may appropriately be a transmitting or reflecting element, as described above relative to the optical element 26.

Similar to the detection assembly 20 described above, the detection assembly 50 desirably may also include or contain suitable control components, such as represented by the box 77 and joined or connected to the birefringent filter 66 as signified by the line 78, such as to one or more produce heat, control the temperature of the instrument and/or tune the transmission of the birefringent filter.

Also similar to the detection assembly 20, the detection assembly 50 may also desirably include or contain suitable components, such as in the form of a display device, represented by the box 79 joined or connected to the detector 74 as signified by the line 79a such as to permit or facilitate the display or readout of a signal representative of the presence of a targeted species in the light path.

FIG. 4 illustrates a simple transverse electro-optic (EO) birefringent filter, generally designated by the reference numeral 80, suitable for use in detection assemblies in accordance with the invention. The electro-optic birefringent filter 80 includes an input polarizer 82 and an output polarizer 84 with an electro-optic birefringent crystal 86 interposed therebetween. The polarization direction associated with the extraordinary index $n_e$ and the ordinary index $n_o$ are shown in FIG. 4 with the voltage applied along the optic axis. The polarizers 82 and 84 are oriented at 45 degrees with respect to the optic axis of the birefringent crystal 86. Those skilled in the art and guided by the teachings herein provided will appreciate that various types or forms of polarizers are available and can be selected for use in the practice of the invention. For example, suitable polarizers for use in the practice of the invention include dichroic, grid and birefringent polarizers.

A voltage, as signified by the +V (with the associated reference numeral 90) and the −V (with the associated reference numeral 92) and such as supplied or provided by means of an AC or DC power supply or transformer, is applied to the crystal 86 such as to induce modulation of the optical transmission by the electric field.

Unlike collimated light birefringent filters in which there is essentially one direction of light for each polarization passing through the birefringent filter, convergent beam birefringent filters in accordance with the invention possess an average phase modulation of the converging optical beam to tune the bandpass of the convergent beam birefringent filter. Such phase modulation represents an integrated or averaged response over the different ray path directions in the cone of light passing through the convergent beam birefringent filter.

While the invention has been described above making reference to a simple transverse electro-optic (EO) birefringent filter 80 having an applied voltage in a transverse direction to the direction of light through the filter, it will be appreciated that the broader practice of the invention is not necessarily so limited. For example, the invention can be practiced wherein voltage is applied in the direction of the light transmission through the filter, if desired.

Further, while the simple transverse electro-optic (EO) birefringent filter 80 described above includes only a single element or stage, as previously described, birefringent filters containing or including multiple elements or stages may, if desired, be used. For example, such multiple element or stage birefringent filter may simply further incorporate or include one or more additional birefringent material elements with additional associated polarizer(s). As identified above, assemblies containing or including such multiple element or stage birefringent filters may be desired, for example, to more specifically limit or restrict the light passed therethrough.

Those skilled in the art and guided by the teachings herein provided will appreciate that the use of a non-collimated convergent light path through the birefringent crystal in accordance with the invention desirably eliminates the need for collimating optics and allows for a higher optical throughput by converging the light onto the detector with a reduced or minimal number of optical elements.

Further, the invention generally provides suitably low power consuming assemblies and methods such as for use in the detection of a target species in a test sample. The invention further generally provides such detection assemblies and methods having either or both a construction and operation of increased or improved simplicity. In view of the above, the invention generally provides such detection assemblies and methods which are desirably conducive to either or both portable and battery-powered operation and use.

A currently perceived advantageous application of the invention is to the detection or sensing of the presence of methane in a sample volume. It is to be understood, however, that the broader practice and use of the detection assemblies and methods herein described are not necessarily limited to the detection or sensing of a particular target species. Thus, the invention can advantageously be applied to the detection or sensing of other target species, as may be desired in particular applications.

The application of the invention to the detection or sensing of the presence of methane in a sample volume will now be more specifically described making specific reference to various of the above-described drawings. In particular, the detection assembly 50, shown in FIG. 3, can advantageously be applied to the spectral identification of methane.

As shown in FIG. 3, the projection optics 56 are provided to project incident radiation in a converging beam from the radiation source 52. Radiation passing through the projection optics 56 is directed to pass through a bandpass or blocking filter 64 and then through the convergent beam birefringent filter 66. As shown in FIG. 4, the birefringent filter may desirably include an input polarizer 82, an output polarizer 84 and a birefringent material 86, e.g., a birefringent crystal, placed between the polarizers 82 and 84.

Returning to FIG. 3, the birefringence of the birefringent filter 66 may be varied or tuned via the birefringence controller 77. Tuning of the birefringent filter 66 causes a time-dependent overlap between the spectral transmission of the convergent beam birefringent filter and the absorption spectrum of the methane. Radiation leaving the birefringent filter 66 is then collected via the detector optics 70 and focused on the detector 74 such as to produce an electronic signal, such as shown or displayed on the display device 79, and such as represents the amount of absorbing species (methane) present in the sample volume.

In accordance with one preferred form of such embodiment, the radiation source 52 is an incandescent lamp, the projection optics 56 is in the form of a single lens, the bandpass filter 64 is a multilayer infrared interference filter, the birefringent filter 66 is composed (referring to FIG. 4) of input and output polarizers 82 and 84 having the form of grid polarizers with a birefringent material 86, such as a lithium niobate birefringent crystal, whose birefringence is tuned electronically via the linear electro-optic effect, interposed therebetween. Further, the electric field can advantageously be applied to such lithium niobate crystal in the transverse mode perpendicular to the direction of the radiation flow through the birefringent filter, i.e., perpendicular to the line joining the center of the entrance face of the lithium niobate crystal and center of the projection lens, such as shown in FIG. 4 as the $n_e$ axis. A preferred detector optics for use in such practice is a single lens. A preferred detector for use in such practice is an indium arsenide photodiode and such as has a high detectivity for radiation having a wavelength near 3.4 microns.

In the typical practice of the invention, important design parameters for such projection optics include the focal length and positioning of the projection lens relative to the radiation source. As will be appreciated by those skilled in the art and guided by the teachings herein provided, such parameters can serve to determine the degree of convergence of the projected converging beam of radiation and the intensity of the radiation entering the birefringent filter. It is generally preferred that the positioning of the projection lens be selected to maximize the useable radiation entering the input aperture of the birefringent filter. Further, the bandpass interference filter can desirably be selected to limit the input spectrum of the radiation to a part of the spectrum of interest, such as in the wavelength range of about 3.1–3.5 micron wavelengths for methane detection. The bandpass filter is preferably placed just before the entrance to the birefringent filter. Also, the focal length and positioning of the lens can advantageously be selected to match the acceptance angle of the birefringent filter.

Further, the detector lens can desirably be positioned directly behind the birefringent filter and have an aperture larger than the birefringent filter such as to permit the effective collection of transmitted radiation. The detector can be optimally placed and positioned to match the size of detector to the radiation converging through the detector lens. In specific applications, the preferred implementation of the detector will typically be dependent on the wavelength range of the radiation: UV, visible, near infrared or far infrared. In the case of methane detection the detector will desirably be sensitive to wavelengths which may be absorbed by methane, such as wavelengths in the range of about 3.1–3.5 microns. As identified above, an indium arsenide photodiode, such as having a high detectivity near 3.4 microns, is a preferred detector for use in such an application.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. A detection assembly comprising:
   a source of convergent electromagnetic radiation spaced apart from a tunable birefringent filter by a sample volume and
   a detector to detect the incidence of electromagnetic radiation of a selected wavelength after passage of convergent electromagnetic radiation through the sample volume and the birefringent filter.

2. The detection assembly of claim 1 wherein the source of convergent electromagnetic radiation comprises:
   a source providing a supply of light and
   a first optical element to direct at least a portion of the supply of light to form a converging beam of light.

3. The detection assembly of claim 2 additionally comprising a filter interposed between the first optical element and the tunable birefringent filter.

4. The detection assembly of claim 3 additionally comprising a second optical element interposed between the birefringent filter and the detector.

5. The detection assembly of claim 1 wherein the tunable birefringent filter comprises at least one birefringent filter stage.

6. The detection assembly of claim 1 additionally comprising a second optical element interposed between the birefringent filter and the detector.

7. The detection assembly of claim 1 comprising means to control the temperature of the birefringent filter.

8. The detection assembly of claim 1 comprising means to produce a signal representative of absorption due to presence of a selected target species in the sample volume.

9. The detection assembly in accordance with claim 8 wherein the selected target species in the sample volume is methane.

10. The detection assembly of claim 1 wherein the tunable birefringent filter is a transverse birefringent filter.

11. The detection assembly of claim 1 wherein the birefringent filter comprises an input and an output polarizer with a birefringent electro-optical material interposed therebetween.

12. The detection assembly of claim 11 wherein the birefringent filter additionally comprises means for applying a voltage to the birefringent electro-optical material to induce a modulating electric field therein.

13. In a method for detecting the presence of a target species in a sample volume wherein light is passed through the sample volume to a birefringent filter, the improvement comprising:
    passing convergent light rays through the sample volume to the birefringent filter.

14. The method of claim 13 wherein light passed through the birefringent filter is incident onto a detector.

15. The method of claim 13 wherein the target species absorbs light in a predetermined spectral region, said method additionally comprising:
    tuning the birefringent filter through the light absorbing predetermined spectral region of the target species.

16. The method of claim 13 additionally comprising:
    producing a signal representing the presence of the target species in the gas sample.

17. The method of claim 13 wherein the birefringent filter comprises an input and an output polarizer with a birefringent electro-optical material interposed therebetween, said method comprising:
    applying a voltage to the birefringent electro-optical material to induce a modulating electric field therein.

18. The method of claim 13 wherein the target species is methane.

19. A method for detecting the presence of a target species in a gas sample, wherein the target species absorbs light in a predetermined spectral region, the method comprising:
    passing convergent light through the gas sample to a birefringent filter and subsequently to a detector,
    tuning the birefringent filter through the predetermined spectral region, and
    producing a signal representing the presence of the target species in the gas sample.

20. The method of claim 19 wherein the target species is methane.

* * * * *